US00PP37006P2

(12) United States Plant Patent
Griffin

(10) Patent No.: US PP37,006 P2
(45) Date of Patent: Oct. 7, 2025

(54) ***AGAVE* PLANT NAMED 'GOLDRUSH'**

(50) Latin Name: *Agave desmettiana*
Varietal Denomination: GOLDRUSH

(71) Applicant: Altman Specialty Plants, Inc, Vista, CA (US)

(72) Inventor: Kelly Griffin, Carlsbad, CA (US)

(73) Assignee: Altman Specialty Plants LLC, Vista, CA (US)

( * ) Notice: Subject to any disclaimer, the term of this patent is extended or adjusted under 35 U.S.C. 154(b) by 0 days.

(21) Appl. No.: 18/985,281

(22) Filed: Dec. 18, 2024

(51) Int. Cl.
*A01H 6/12* (2018.01)
*A01H 5/12* (2018.01)

(52) U.S. Cl.
USPC ..... Plt./373

(58) Field of Classification Search
USPC ..... Plt./373
See application file for complete search history.

(56) References Cited

U.S. PATENT DOCUMENTS

PP34,229 P2 * 5/2022 Hansen ..... A01H 6/12
Plt./373

* cited by examiner

*Primary Examiner* — Karen M Redden
(74) *Attorney, Agent, or Firm* — Cassandra Bright

(57) ABSTRACT

A new and distinct *Agave* cultivar named 'GOLDRUSH' is disclosed, characterized by a distinctive wide bright yellow margin up to one inch thick. Plants have a vigor similar to unvariegated plants. Foliage is glossy and shiny. The variegation pattern is stable and consistent though production of multiple generations. The new variety is an *Agave,* typically produced as a garden or container plant.

2 Drawing Sheets

Latin name of the genus and species: *Agave desmettiana.*
Variety denomination: 'GOLDRUSH'.

BACKGROUND OF THE INVENTION

The new cultivar is a product of chance discovery. The new variety was selected as a single plant naturally occurring mutation in a group of tissue culture stock plants. The parent plant is the unpatented species *Agave desmettiana.* The discovery was made at a commercial laboratory in Escondido, California during October of 2012.

Asexual reproduction of the new cultivar 'GOLDRUSH' was first performed by tissue culture at a commercial laboratory in Escondido, California in 2015. 'GOLDRUSH' has since produced several generations and has shown that the unique features of this cultivar are stable and reproduced true to type.

SUMMARY OF THE INVENTION

The cultivar 'GOLDRUSH' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'GOLDRUSH.' These characteristics in combination distinguish 'GOLDRUSH' as a new and distinct *Agave* cultivar:

1. Distinctive variegation; wide bright yellow margins of up to one inch thick.
2. Vigorous growth similar to unvariegated plants.
3. Glossy, shiny foliage.

4. Stable variegation pattern.
5. Consistent production through multiple generations.

PARENTAL COMPARISON

Plants of the new cultivar 'GOLDRUSH' are similar to the parent in most horticultural characteristics. However, plants of the new variety differ from the seed parent in the following:

1. The new variety has a distinct, thick yellow margin not found on the parent.

COMMERCIAL COMPARISON

'GOLDRUSH' can be compared to the unpatented commercial variety *Agave desmettiana* 'Variegated'. The two *Agave* varieties are similar in most horticultural characteristics; however, the new variety differs in the following:

1. The new variety has a thicker, brighter yellow foliar margin than this comparator.
2. The new variety has an overall brighter appearance than this comparator as it does not have a glaucous layer muddling the coloration.

'GOLDRUSH' can also be compared to the unpatented commercial variety *Agave desmettiana* 'Desert Sunset', unpatented. The two *Agave* varieties are similar in most horticultural characteristics; however, the new variety differs in the following:

1. The new variety has a brighter yellow foliar margin than this comparator.
2. The new variety has an overall brighter appearance than this comparator as it does not have a matte, glaucous layer muddling the coloration.

BRIEF DESCRIPTION OF THE PHOTOGRAPHS

Figure 1:
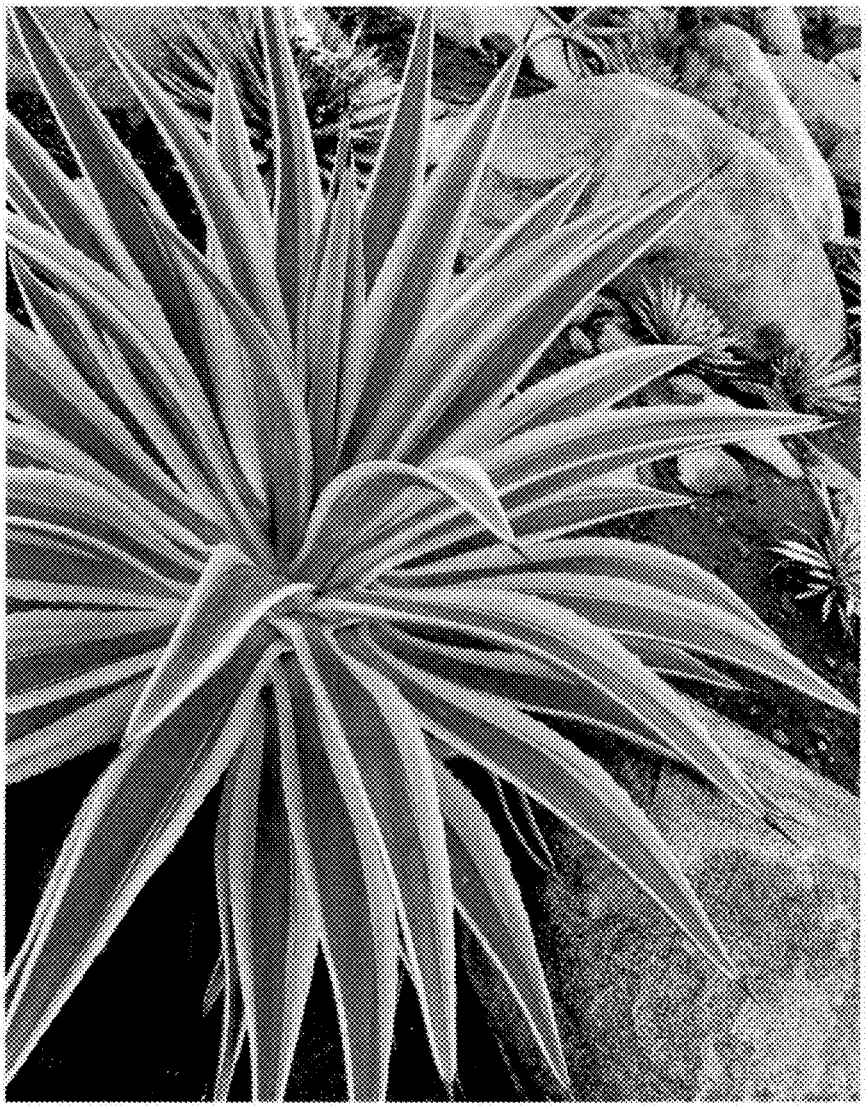

The accompanying photograph in FIG. 1 illustrates in full color a typical plant of 'GOLDRUSH' grown outdoors in Carlsbad, California. This plant is approximately 2 years old.

Figure 2:
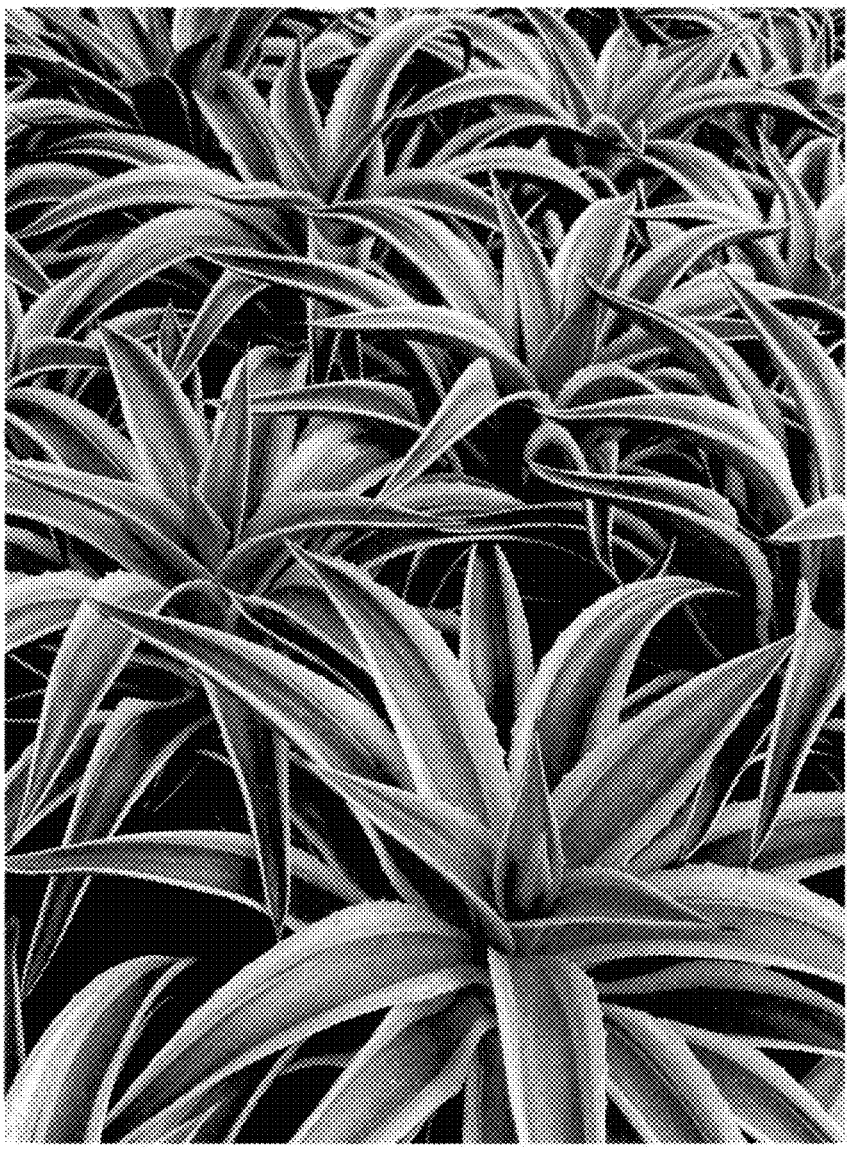

FIG. 2 illustrates multiple plants of the new variety, all with consistent bright yellow margins.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2007 edition, except where general terms of ordinary dictionary significance are used. The following observations and measurements describe 'GOLDRUSH' plants in a commercial greenhouse in Vista, California. Temperatures ranged from 21° C. to 25° C. during the day, and 8° C. to 19° C. during the night. No artificial light, photoperiodic treatments or chemical treatments were given to the plants. Natural light conditions were approximately 2500 to 3000 fc of light. Measurements and numerical values represent averages of typical plant types.

Botanical classification: *Agave desmettiana* 'GOLDRUSH.'

Age of the plant described: About 3 years.

PROPAGATION

Time to initiate roots: Approximately 25 days at 22° C.

Root description: Fibrous. Brown, not accurately measured with the R.H.S. chart.

Propagation method: Tissue culture.

PLANT

Growth habit: Upright rosette.

Container size: 5-gallon.

Height: Approximately 20 cm.

Plant spread: Approximately 35 cm.

Growth rate: Moderate. Compared to typical variegated *Agaves,* rapid.

FOLIAGE

Leaf:

*Arrangement.*—Rosette.

*Average length.*—15-18 cm.

*Average width.*—4 cm at widest section, 1.0 cm near apex.

*Shape of blade.*—Lanceolate.

*Apex.*—Acute, sharp.

*Base.*—Truncate, non-clasping Margin: Dentate. Moderate density of dentations, average 1 cm apart along majority of leaf blade, sparse or absent near apex. Dentations are somewhat sharp.

*Texture of top surface.*—Smooth.

*Texture of bottom surface.*—Smooth.

*Appearance of top surface.*—Glossy, bright.

*Texture of bottom surface.*—Somewhat glossy.

*Quantity of leaves.*—Approximately 20 to 25.

*Color.*—Young foliage upper side: Near RHS Green 138A. Margin about 5 to 10 mm, near Yellow 2B. Young foliage under side: Near RHS Green 138A. Margin about 5 to 10 mm, near Yellow-Green 154C. Mature foliage upper side: Near RHS Green 138A. Margin about 10 to 25 mm, near Yellow 7C. Mature foliage under side: Near RHS Green 138A. Margin about 10 to 25 mm, near Yellow 7D.

*Venation.*—Linear. Color: Indistinguishable from leaf blade.

FLOWER

Not observed to date.

REPRODUCTIVE ORGANS

Not observed to date.

OTHER CHARACTERISTICS

Seeds and fruits: Not observed to date.

Temperature tolerance: USDA Zones 8 to 10.

Disease/pest resistance: Neither resistance nor susceptibility to the normal diseases and pests of *Agave* observed.

What is claimed is:

1. A new and distinct cultivar of *Agave* plant named 'GOLDRUSH' as herein illustrated and described.

* * * * *